United States Patent
Hossack et al.

(10) Patent No.: US 10,052,082 B2
(45) Date of Patent: *Aug. 21, 2018

(54) APPARATUS AND METHOD FOR USE OF RFID CATHETER INTELLIGENCE

(71) Applicant: Volcano Corporation, San Diego, CA (US)

(72) Inventors: Norman Hugh Hossack, Folsom, CA (US); Stephen Charles Davies, Folsom, CA (US); Donald Mamayek, Mountain View, CA (US); Richard Scott Huennekens, San Diego, CA (US); Stephen M. Fry, El Dorado Hills, CA (US); Eric Vaughn Mott, Rancho Cordova, CA (US); Peter Smith, Sacramento, CA (US); Scott Tennant Brownlie, Carmichael, CA (US); Jon David Klingensmith, El Dorado Hills, CA (US); Richard Chester Klosinski, Jr., Carmichael, CA (US); Edward Anthony Oliver, Folsom, CA (US); Masood Ahmed, Rocklin, CA (US); Gerald Lea Litzza, Sacramento, CA (US)

(73) Assignee: Volcano Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/821,185

(22) Filed: Aug. 7, 2015

(65) Prior Publication Data
US 2015/0342564 A1    Dec. 3, 2015

Related U.S. Application Data

(63) Continuation of application No. 13/182,067, filed on Jul. 13, 2011, now Pat. No. 9,101,298, which is a
(Continued)

(51) Int. Cl.
*A61B 8/12* (2006.01)
*A61B 1/00* (2006.01)
(Continued)

(52) U.S. Cl.
CPC ............ *A61B 8/12* (2013.01); *A61B 1/00059* (2013.01); *A61B 8/4438* (2013.01); *A61B 8/4472* (2013.01); *G06K 19/07749* (2013.01)

(58) Field of Classification Search
CPC ..... A61B 1/00059; A61B 8/12; A61B 8/4438; A61B 8/4472; G06K 19/07749
See application file for complete search history.

(56) References Cited

U.S. PATENT DOCUMENTS

| | | | |
|---|---|---|---|
| 4,868,476 A * | 9/1989 | Respaut | G10K 11/355 |
| | | | 318/490 |
| 5,487,386 A | 1/1996 | Wakabayashi | |

(Continued)

FOREIGN PATENT DOCUMENTS

| | | |
|---|---|---|
| EP | 1550465 A1 | 7/2005 |
| JP | H 11-226017 | 8/1999 |

(Continued)

OTHER PUBLICATIONS

International Search Report for PCT/US06/39985 dated Aug. 16, 2007.
(Continued)

*Primary Examiner* — Katherine Fernandez

(57) ABSTRACT

A method and system is provided for using backscattered data and known parameters to characterize vascular tissue. Specifically, methods and devices for identifying information about the imaging element used to gather the backscattered data are provided in order to permit an operation console having a plurality of Virtual Histology classification trees to select the appropriate VH classification tree for
(Continued)

analyzing data gathered using that imaging element. In order to select the appropriate VH database for analyzing data from a specific imaging catheter, it is advantageous to know information regarding the function and performance of the catheter, such as the operating frequency of the catheter and whether it is a rotational or phased-array catheter. The present invention provides a device and method for storing this information on the imaging catheter and communicating the information to the operation console. In addition, information related to additional functions of the catheter may also be stored on the catheter and used to further optimize catheter performance and/or select the appropriate Virtual Histology classification tree for analyzing data from the catheter imaging element.

22 Claims, 6 Drawing Sheets

Related U.S. Application Data continuation of application No. 11/250,159, filed on Oct. 12, 2005, now Pat. No. 7,988,633.

(51) Int. Cl.
*A61B 8/00* (2006.01)
*G06K 19/077* (2006.01)

(56) References Cited

U.S. PATENT DOCUMENTS

| | | | |
|---|---|---|---|
| 5,544,660 A | 8/1996 | Crowley | |
| 6,004,271 A * | 12/1999 | Moore | A61B 8/12 600/445 |
| 6,036,654 A | 3/2000 | Quinn | |
| 6,152,878 A | 11/2000 | Nachtomy et al. | |
| 6,248,083 B1 | 6/2001 | Smith | |
| 6,266,551 B1 | 7/2001 | Osadchy | |
| 6,270,460 B1 | 8/2001 | McMartin | |
| 6,273,858 B1 | 8/2001 | Fox et al. | |
| 6,308,089 B1 | 10/2001 | Von der Ruhr | |
| 6,387,092 B1 | 5/2002 | Burkside | |
| 6,547,757 B1 | 4/2003 | Kranz et al. | |
| 6,578,579 B2 | 6/2003 | Burnside | |
| 6,611,793 B1 | 8/2003 | Burnside et al. | |
| 6,651,669 B1 | 11/2003 | Burnside | |
| 6,659,940 B2 | 12/2003 | Adler | |
| 6,733,495 B1 * | 5/2004 | Bek | A61B 18/00 606/1 |
| 6,792,390 B1 | 9/2004 | Burnside | |
| 6,847,490 B1 | 1/2005 | Nordstrom | |
| 6,861,954 B2 | 3/2005 | Levin | |
| 6,985,870 B2 | 1/2006 | Martucci | |
| 7,840,254 B2 | 11/2010 | Glossop | |
| 7,914,458 B2 | 3/2011 | Hossack et al. | |
| 7,988,633 B2 * | 8/2011 | Hossack | A61B 1/00059 600/437 |
| 9,101,298 B2 * | 8/2015 | Hossack | A61B 1/00059 |
| 2003/0183683 A1 | 10/2003 | Stewart | |
| 2004/0008123 A1 | 1/2004 | Carrender | |
| 2004/0122326 A1 | 6/2004 | Nair et al. | |
| 2004/0172016 A1 | 9/2004 | Bek | |
| 2004/0203478 A1 * | 10/2004 | Scott | G06K 7/0008 455/70 |
| 2004/0230116 A1 | 11/2004 | Cowan | |
| 2004/0231772 A1 | 11/2004 | Leonard | |
| 2005/0071746 A1 * | 3/2005 | Hart | G06F 3/1206 715/200 |
| 2005/0149358 A1 | 7/2005 | Sacco | |
| 2005/0159802 A1 | 7/2005 | Furst | |
| 2005/0196026 A1 | 9/2005 | Klingensmith et al. | |
| 2005/0277873 A1 | 12/2005 | Stewart | |
| 2006/0065713 A1 | 3/2006 | Kingery | |

FOREIGN PATENT DOCUMENTS

| | | | |
|---|---|---|---|
| JP | 2003-061975 | | 3/2003 |
| JP | 2004-530315 | | 9/2004 |
| JP | 2006-506128 | | 2/2006 |
| WO | WO 02/41941 | | 5/2002 |
| WO | WO2004/043256 | * | 5/2004 |
| WO | WO 2004/043256 | | 5/2004 |

OTHER PUBLICATIONS

Written Opinion for PCT/US06/39985 dated Aug. 16, 2007.
Japanese Office Action and Translation received in Japanese Application No. 2011-163187, dated Jul. 31, 2012, 2 pages.
Japanese Final Office Action and Translation received in Japanese Application No. 2011-163187, dated Mar. 25, 2014, 7 pages.
Japanese Office Action and Translation received in Japanese Application No. 2006-092291, dated Apr. 26, 2011, 4 pages.
Japanese Final Office Action and Translation received in Japanese Application No. 2006-092291, dated Jul. 3, 2012, 4 pages.
Extended European Search Report received in European Application No. 06825868.0, dated Jan. 24, 2013, 8 pages.
European Office Action received in European Application No. 06825868.0, dated Feb. 11, 2014, 6 pages.

* cited by examiner

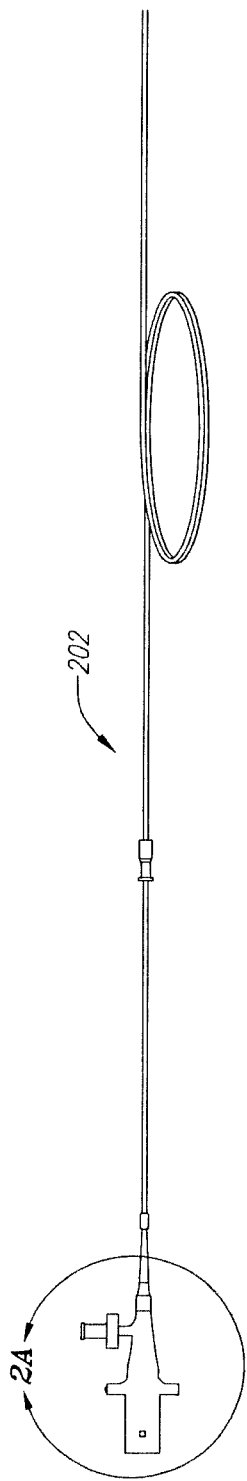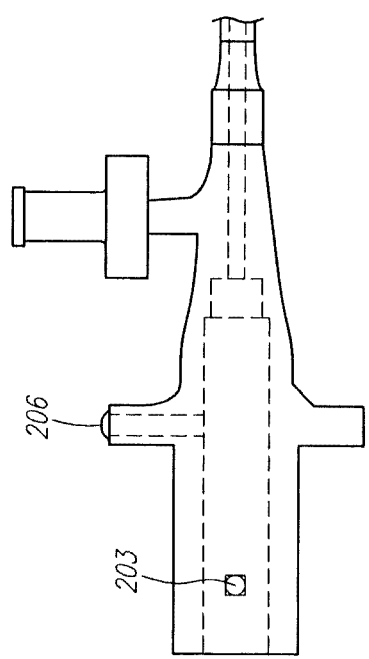

APPARATUS AND METHOD FOR USE OF RFID CATHETER INTELLIGENCE

CROSS-REFERENCE TO RELATED APPLICATIONS

This application is a continuation of U.S. patent application Ser. No. 13/182,067, filed Jul. 13, 2011, now U.S. Pat. No. 9,101,298, which is a continuation of U.S. patent application Ser. No. 11/250,159, filed Oct. 12, 2005, now U.S. Pat. No. 7,988,633, both of which are hereby incorporated by reference in their entireties.

FIELD OF THE INVENTION

The present invention relates to a system and method, of using backscattered data and known parameters to identify and characterize vascular tissue, or more particularly, to devices and methods of use for identifying the operating frequency and type of catheter being used to acquire the backscattered data and for relaying specific information about the catheter to an attached operation console.

BACKGROUND OF THE INVENTION

Ultrasound imaging of the coronary vessels of a patient can provide physicians with valuable information regarding the identify the shape of a blood vessel, its density, its composition that can be useful in the diagnosis and/or treatment of a patient. For example, such information may show the extent of a stenosis in a patient, reveal progression of disease, determine the vulnerability of the atherosclerotic plaque for causing myocardial infarction, help determine whether procedures such as angioplasty, stenting or atherectomy are indicated, or whether more invasive procedures are warranted.

Currently, intravascular ultrasound (IVUS) devices use reflected ultrasound data to reproduce or image a blood vessel. In a typical ultrasound imaging system, an ultrasonic transducer is attached to the end of a catheter that is carefully maneuvered through a patient's body to a point of interest such as within a blood vessel. The transducer may be a single-element crystal or probe that is mechanically scanned or rotated back and forth to cover a sector over a selected angular range. Acoustic signals are then transmitted and echoes (or backscatter) from these acoustic signals are received. As the probe is swept through the sector, many acoustic lines are processed building up a sector-shaped image of the patient. These signals may then be processed using well known techniques and transformed into a gray scale image of the vasculature on a computer console in the catheter lab, i.e. an IVUS image.

More recently, the radio frequency signal from the backscatter data has been gathered and correlated with known histology data to permit further analysis and classification of the vasculature. This new Virtual Histology™ technology provides the ability to identify boundary features within the vasculature and plaque and to determine the composition of each patient's atherosclerotic plaques from the RF backscatter data. Currently, Virtual Histology mapping is accomplished by transforming the RF backscatter signal from an IVUS catheter into the frequency domain and then analyzing various power spectral characteristics to classify tissue in windows along each IVUS scan line according to a database, or classification tree, containing the specific spectrum RF signals for four plaque types, fibrous, fibro-fatty, dense calcium and necrotic core. Using this technology, Virtual Histology™ (VH) images generated from IVUS data can now show four plaque component types.

The VH databases, or classification trees, used to correlate the patient's IVUS data and identify tissue type are compiled by examining RF backscatter data from known histologic tissue types and correlating the spectral characteristics of the backscatter data with a specific tissue type. However, the VH classification trees must be computed using IVUS catheters operating at a specific frequency since data obtained using catheters operating at other frequencies may result in different spectral characteristics for a given tissue. Thus, separate VH classification trees must be generated for each catheter operating frequency and the patient data obtained from a catheter operating at a specific frequency must be correlated with the classification tree for that operating frequency in order to achieve an accurate mapping of the patients vasculature and classification of the vascular tissue and plaque type. Currently IVUS catheters operating at 20 MHz, 30 MHz and 40 MHz are commercially available. In addition, there are several types of ultrasonic transducers capable of gathering and transmitting the frequency spectrum of RF signal backscattered from vascular tissue needed to characterize the vascular tissue. For example, phased array IVUS catheters or rotational IVUS catheters, such as those disclosed in such as disclosed in U.S. Pat. No. 5,368,037, issued to Eberle and U.S. Pat. No. 5,000,185, issued to Yock, both fully incorporated herein by reference, may be used to gather RF data. However, once again, different VH classification trees must be generated for data obtained from phased array vs. rotational IVUS catheters.

Early imaging catheters typically relied on manual recognition of a catheter type. For example, catheters were color coded according to type then the operator had to manually input this information into an operation console. Other early alternatives included measuring the catheter resistance to determine the operating frequency or storing catheter information in an EPROM located in the catheter connector. However, with the use of multiple VH classification databases to analyze data from catheters with different operating frequencies or modes of use, the identification and communication of catheter operating information from the catheter to the operation console is critical.

Thus, new devices and methods are needs for identifying information regarding the IVUS catheter being used, for example the catheter type, operational frequency, individual performance characteristics and/or calibration coefficients, etc, and relaying that information to an attached operator's console to assist in selection of the appropriate VH classification tree for analyzing the RF data obtained from the IVUS catheter.

SUMMARY OF THE INVENTION

The present invention provides a method and devices for communication between an imaging catheter and an operation console to select the appropriate VH classification database. In order to select the appropriate VH database for analyzing data from a specific imaging catheter, it is advantageous to know information regarding the operating frequency of the catheter and whether it is a rotational or phased-array catheter. However, additional information regarding specific catheter performance characteristics such as the unity gain value, the boot mode, the catheter sensitivity may also be stored on the catheter and used to further optimize catheter performance and/or select the appropriate VH tree for analyzing data from the catheter imaging element.

In an embodiment according to the present invention, a Radio Frequency Identification (RFID) chip, such as a Maxwell ME1 or ME2 RFID chip, mounted on a connector on the proximal end of the catheter, is used to store information about the catheter. RFID technology is a wireless technology for data transfer previously used in applications, such as electronic toll collection, railway car identification and tracking, that offers automatic identification functionality as well as the ability to easily and securely store, transfer and update information. RFID provides certain advantages over prior catheter identification systems. For example, the RFID chip may have a memory capacity of several kilobytes or more, which is substantially greater than the maximum amount of data that may be acquired from the prior methods of catheter identification. The information initially stored on the RFID tag may include identifying information about the catheter such as make, model and serial number, operational characteristics of the catheter, such as operating frequency, type of imaging element, calibration coefficients, sensitivity, and boot mode, and use limitations, such as expiration date, geographic region of use, permissible number of uses or permissible time of use. In addition, the short transmission distance of the RFID chip may avoid interfering with other electronic equipment in the cath lab.

The RFID technology may also include an antenna capable of reading and writing additional information to the chip. In such an embodiment, the information regarding the catheter may be updated, for example, as the catheter is used and the performance characteristics and/or calibration coefficients for a given operating frequency or catheter model change.

The catheter interface device includes an RFID scanner mounted in proximity to the connector on the interface device for the catheter. In an embodiment according to the present invention, the catheter interface device may be a pull back device used to operate an IVUS catheter. Here, the RFID scanner is mounted so that when the catheter connector and the pullback device connector are joined the RFID scanner is located within the given transmitting distance for the RFID chip on the catheter, for example between about 0-10 mm. When the catheter is connected to the pullback device, the catheter connector triggers a trip switch located in the interface device connector and activates the RFID scanner. The RFID scanner may then read the information on the catheter RFID chip to determine the identity of the catheter. The interface device may then relay the catheter identification information to the operation console. The interface device may be connected to the operation console via any suitable communication protocol, for example via a USB or serial connection. Once the interface device relays the information to the operation console, the interface device may turn off the RFID scanner.

The information relayed to the operation console may include one or more of the catheter serial number, catheter name, catheter model number, calibration coefficients, time gain control, post amp gain, date of first use, date of last use, number of times used, number of permissible uses, geographic location of permissible use, boot mode, pulse width, or expiration date of the catheter to the operation console. The operation console may then use this information to determine which of the multiple VH classification databases stored on the operation console should be used to analyze the data captured using this catheter and imaging element. For example, the operation console may choose the VH classification tree based on the operating frequency of the attached catheter. Alternatively, the catheter RFID chip may contain additional information regarding sensitivity of the catheter, in which case, the operation console may choose a VH classification tree based on operating frequency of the catheter and a high, medium or low sensitivity rating. In an alternative embodiment, once the operation console has selected a VH classification tree using information stored on the catheter RFID chip, the operation console may use additional information relayed from the catheter RFID chip, such as boot mode, time gain control, post amp gain or other calibration coefficients to further optimize the catheter performance and data analysis.

In addition, the operation console may use the information from the catheter RFID chip to determine whether or not to permit catheter operation. In an alternative embodiment, the catheter RFID chip may further store a security code for the catheter. This security code may be read by the RFID reader on the interface device and if the catheter security code is not authorized for use with the connected catheter interface device, the system will not permit the catheter use. In an alternative embodiment, the catheter RFID chip may further store an expiration date. This expiration date may be read by the RFID reader on the interface device and if the expiration date had passed, the interface device may prohibit catheter use. In another alternative embodiment, the RFID chip may be programmed to permit a given number of uses or hours of use. Here, the RFID chip may be updated after each use to store the total number of uses or total hours of use. When the catheter is connected to an interface device, the interface device may read and compare the values for the permissible hours of use/times used with the total hours of use/times used. Once the total number of uses or total hours of use surpasses the pre-programmed limit, the interface device may prohibit catheter use.

In an alternative embodiment, the RFID scanner located on the interface device may further include RFID read and write capabilities. Here, the operation console may instruct the interface device to turn on the RFID scanner at the end of a catheter use to download information regarding the catheter use to the RFID chip. For example, the operation console may download patient identification, hospital information and operating physician information to the RFID chip. In addition, it is envisioned that at the completion of a clinical procedure, the Virtual Histology images themselves may be downloaded and stored on the catheter RFID chip along with the patient information and used as a medical record of the procedure. The RFID chip may also be designed so that it can be removed in order to provide an easily transportable record of the complete procedure that may used with another with another RFID reader to transfer the information to a different storage medium or analysis device.

In an alternative embodiment, the RFID scanner may also be used to update the operational and performance characteristics and use information of the catheter for future catheter use. When more than a single use is permissible, the catheter may have a shield, for example lead, positioned over the RFID chip to protect the RFID chip during a severe sterilization process, such as radiation. In addition, if upon removal it is desired that the RFID chip be sterile, for example for transfer at bedside, the RFID chip may be presterilized using gas and sealed hermetically prior to positioning the shield.

A more complete understanding of the method and system for vascular tissue characterization will be afforded to those skilled in the art, as well as a realization of additional advantages and objects thereof, by a consideration of the following detailed description of the preferred embodiment. Reference will be made to the appended sheets of drawings, which will first be described briefly.

BRIEF DESCRIPTION OF THE DRAWINGS

FIG. 2 illustrates an embodiment of a catheter for use according to the present invention FIG. 2A illustrates an embodiment of a catheter connector containing an RFID chip for use according to the present invention.

DETAILED DESCRIPTION OF THE INVENTION

Figure 1:
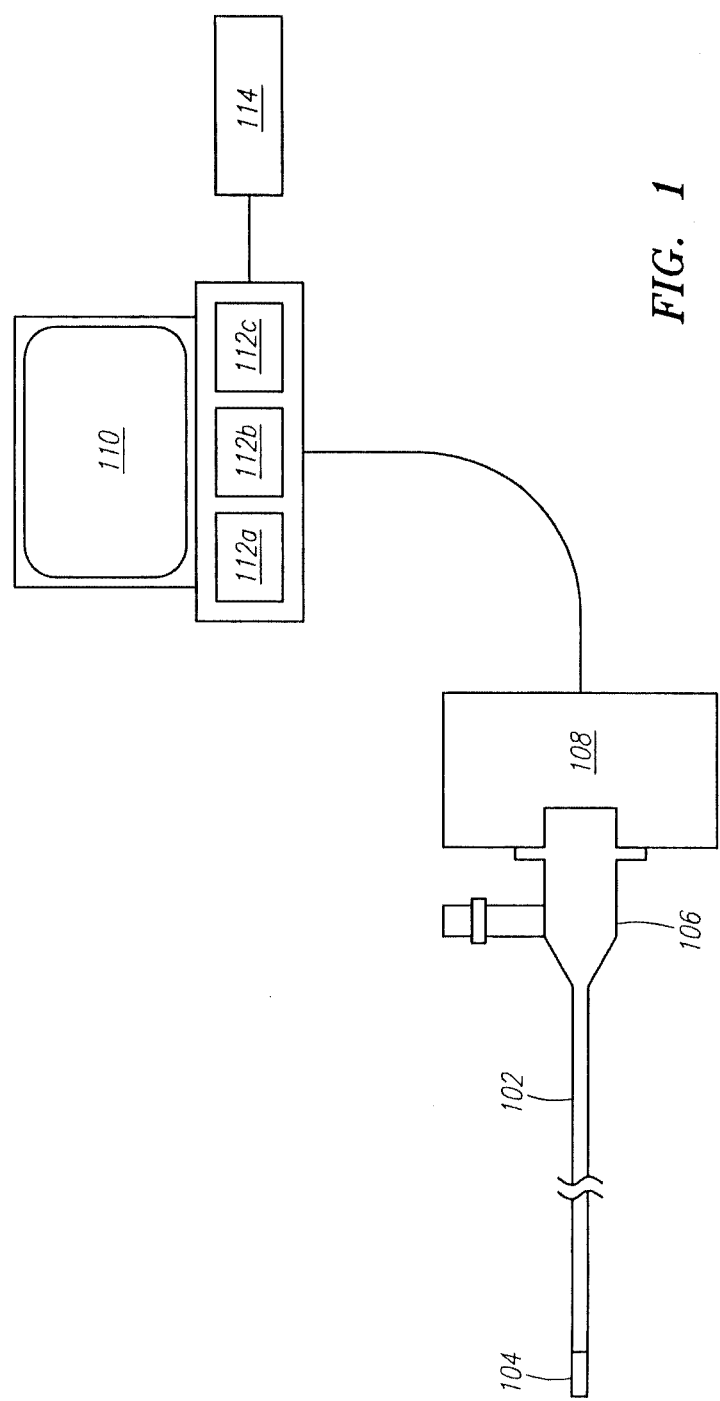
FIG. 1 is a block diagram depicting a system for vascular tissue characterization according to the present invention.

FIG. 1 is a block diagram showing an embodiment of a system for characterizing vascular tissue data. The system generally comprises a catheter 102, having an imaging element 104 operably connected at the distal end, connected to an interface device 108 which is then connected to an operation console 110. When the catheter 102 is connected to the interface device 108, the interface device 108 is triggered and begins reading catheter information stored on a memory device, for example an EPROM, an RFID chip or other suitable memory device, located on the catheter 102. The catheter 102 relays information about the imaging element 104 to the interface device 108. At a minimum, the catheter may communicate the type of imaging element, for example phased array ultrasonic transducers or rotational ultrasonic transducers, and operating frequency of the imaging element. However, the catheter may also relay additional information regarding specific catheter identification and/or performance characteristics, for example catheter serial number, name, make or model, calibration coefficients, imaging element sensitivity, time gain control, post amp gain, date of first use, date of last use, number of times used, number of permissible uses, geographic location of permissible use, boot mode, pulse width, or expiration date of the catheter to the operation console.

The interface device 108 then relays the catheter information to the operation console 110. The interface device 108 may be connected to the operation console 110 via any suitable communication protocol known in the art, for example USB or Serial. In an alternative embodiment, the catheter may be directly connected to the operation console. In another alternative embodiment, the information transfer may be via a wireless communication protocol. The operation console 110 contains a plurality Virtual Histology classification trees 112a-c each developed using known method of comparing histology data and IVUS data gathered by different types of catheters operating at different frequencies.

Currently, Virtual Histology classification trees are developed by collecting and correlating RF backscatter signal from an IVUS catheter with known histologic tissue types as disclosed in U.S. patent application Ser. No. 10/647,971, fully incorporated herein by reference. The RF data is transformed in to the frequency domain and the various power spectral characteristics of the backscattered signal are correlated with characterization data to determine signature parameters for each tissue type. However, these spectral characteristics of the tissue types vary for catheters operating at different frequencies and thus separate classification trees must be used. Accordingly, specific information about the catheter used for a clinical procedure is needed to select the appropriate classification tree for analyzing that data.

The information from the catheter, at a minimum the operating frequency of the connected catheter 102, is used by the operation console 110 to select the appropriate VH classification tree 112a-c for analyzing incoming IVUS data. In addition, information regarding specific catheter performance characteristics such as the unity gain value, the boot mode, the catheter sensitivity may also be stored on the catheter and used to further select the appropriate VH tree for analyzing data from the catheter imaging element. For example, it is envisioned that the operation console 110 could store VH classification trees for low, medium and high sensitivity catheters in each operating frequency. Then, based on information from the catheter regarding the operating frequency and sensitivity of the catheter, the operation console further tailor the selection of the appropriate VH classification tree. In an alternative embodiment, the VH classification tree for the specific catheter may be stored on the catheter. Here, when the catheter is placed in communication with the interface device, the catheter will relay the specific classification tree to use for analyzing the data it collects to the operation console and the operation console will simply download the classification tree from the catheter.

Once the clinical procedure is complete, the operation console 110 may download the VH image and data to the catheter for storage within the catheter memory device and either the entire catheter, the catheter connector containing the RFID chip or the removable RFID chip may then be used as a portable medical record. Alternatively, if the catheter is approved for reuse, the operation console may down load specific information regarding the time and duration of use of the clinical procedure to the catheter. This information may be stored and tracked on the catheter monitor and limit the number of uses or hours of use to a predetermined amount also stored on the catheter.

Figure 2B:
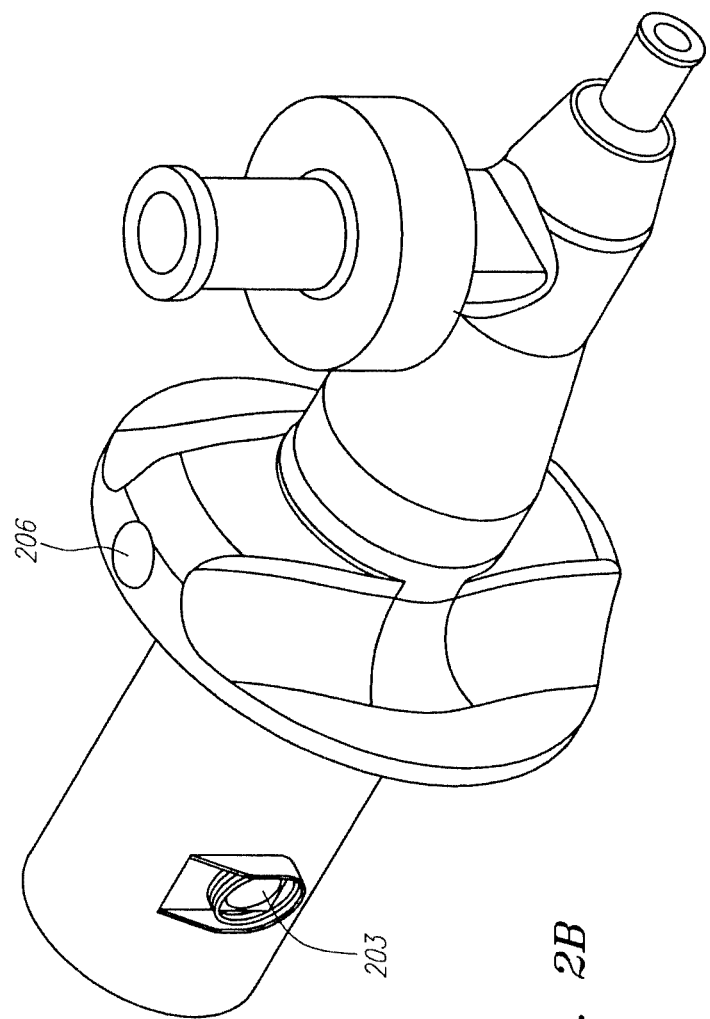
FIG. 2B illustrates an embodiment of a catheter connector containing an RFID chip for use according to the present invention.
Figure 3:
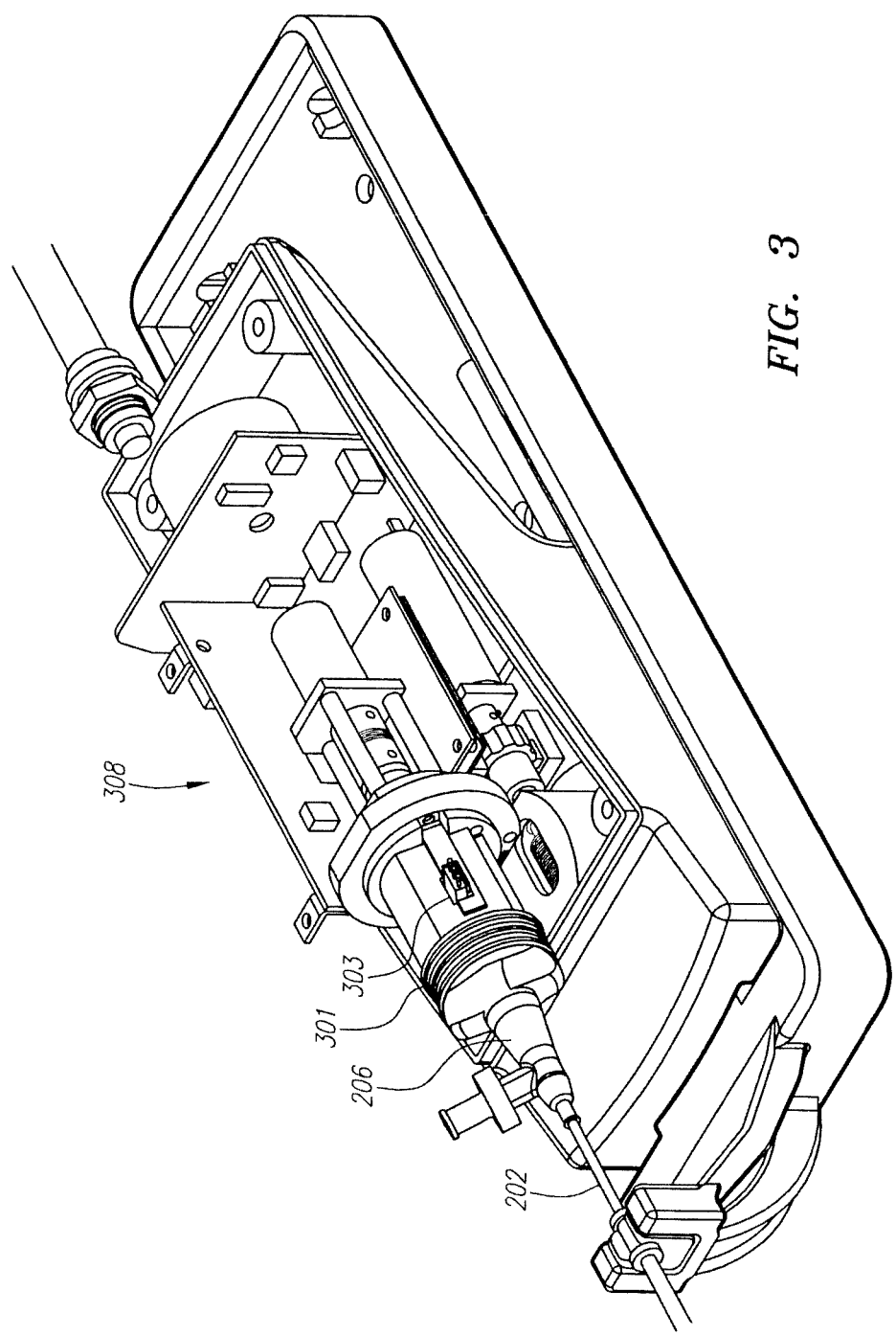
FIG. 3 illustrates an embodiment of a pull back device for use according to the present invention.
Figure 3A:
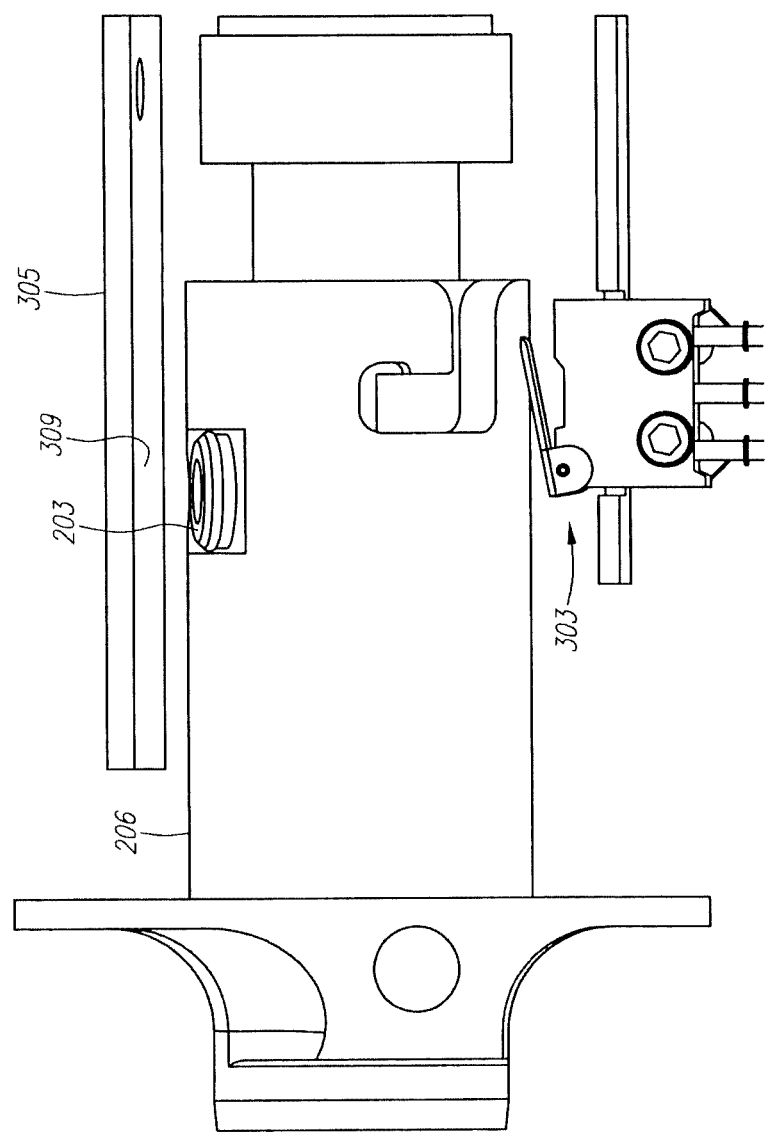
FIG. 3a illustrates an embodiment of a pull back device for use according to the present invention.

In one embodiment according to the present invention, as shown in FIG. 2-3, the catheter 202 may have an RFID chip 203, such as Maxwell ME1 or ME2 RFID chip, mounted on the connector 206 on the proximal end of the catheter 202 for storing information and communicating with the interface device 308. In an alternative embodiment, the catheter may have a second RFID chip (not shown) mounted 180 degrees from the first RFID chip 203 of the connector 206 so catheter can be connected to interface device at more than one circumferential orientation. The RFID chip 203 may have a memory of 128 bytes, alternatively 1K byte, alternatively 2K bytes alternatively 4K bytes to store catheter specific information, including for example catheter serial number, name, make or model, calibration coefficients, imaging element sensitivity, time gain control, post amp gain, number of permissible uses, geographic location of permissible use, boot mode, pulse width, or expiration date of the catheter. Here, when the catheter connector 206 is inserted into the connector 301 on the interface device, the catheter connector 206 engages a trip switch 303 which activates the RFID circuit board 305 to start the RFID scanner 309 looking for the catheter RFID chip 203. The RFID scanner 309 is located near the connection point of two connectors. Thus, when the connectors 206 and 301 are properly joined, the RFID scanner will be with in transmission distance, about 0-10 mm, alternatively about 0-3 mm, from the RFID chip 203 located on the catheter connector 206. The RFID scanner 309 reads the information stored on the catheter RFID chip 203 and relays this information to the RFID circuit board 305. The RFID circuit board 305 may optionally include a microprocessor and instructions for processing and acting on some of the data received from the catheter RFID chip 203. For example, the catheter RFID chip 203 may transmit a security code which must be matched by a corresponding security code on the interface device in order to authorize catheter use. In addition, the RFID scanner 309 may have read and write capability, in which case the RFID circuit board 305 may further include instructions for writing additional information to the catheter RFID chip 203. This information could be useful for tracking the catheter and for ensuring security and sterility of the catheter. For example, the RFID circuit board 305 may receive information from the operation console regarding the patient identification, hospital, operating physician, which could be downloaded and stored on the RFID chip 203. In addition, it is envisioned that at the completion of a clinical procedure, the Virtual Histology images themselves, along with the corresponding patient information may be downloaded and stored on the catheter RFID chip which may then be removed from the catheter and used as a medical record of the procedure. Alternatively, information regarding the time of use, duration of the procedure and interface device used could be downloaded to the RFID chip to monitor and manage sterility of the catheter. For example, once a catheter is connected to a particular interface device, then the catheter will only operate with that interface device for a limited time period, such as 8 hours, or 12 hours or the typical length of a given procedure. The operation console can monitor the duration of use of the catheter and download this information to the catheter RFID chip so that if the catheter is plugged into another interface device, use will not be permitted. If the catheter fails during use, the operation console may also download a failure code as well as complete information regarding the circumstances of the failure to the RFID chip.

Figure 4:
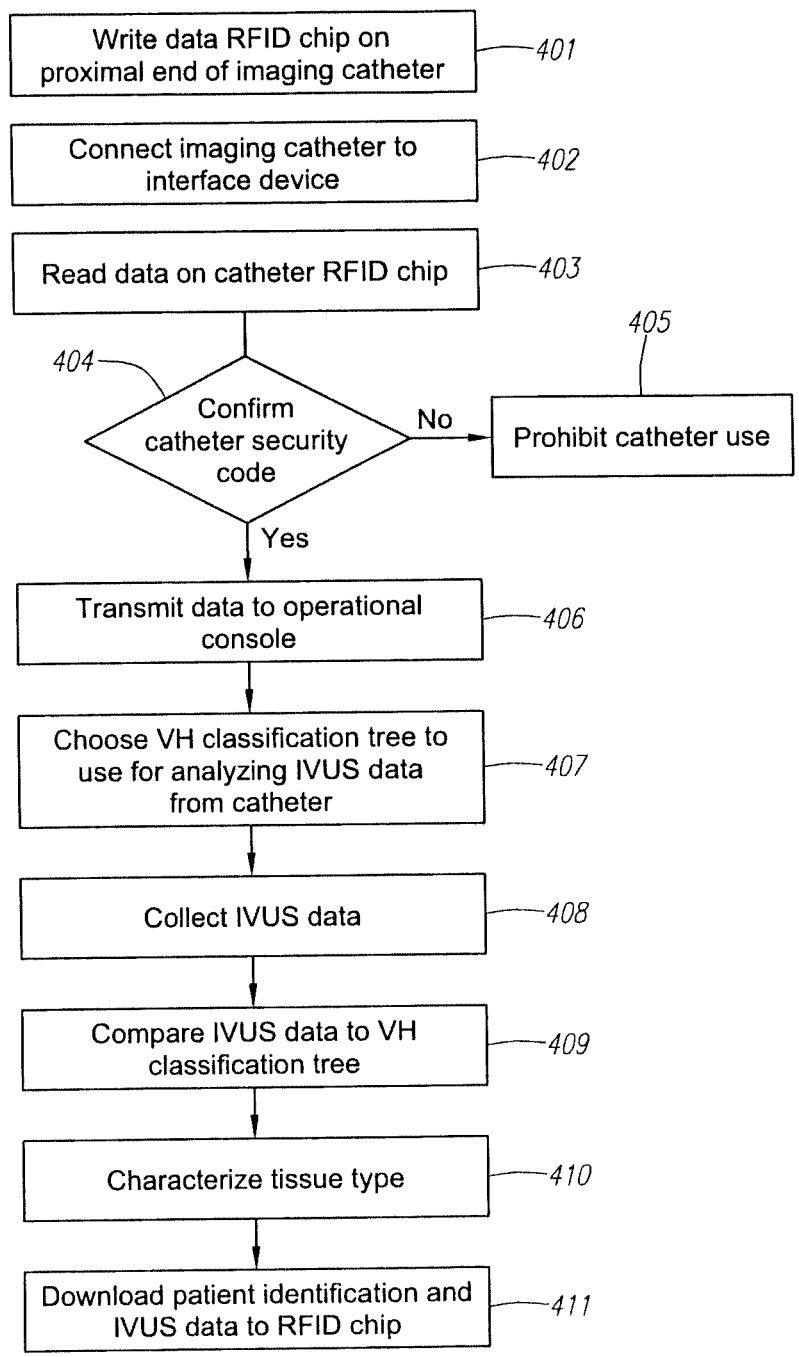
FIG. 4 is a flow chart illustrating exemplary steps for identifying an imaging catheter and selecting the appropriate classification tree for analyzing data from the attached catheter

FIG. 4 shows exemplary steps of a method for characterizing vascular tissue data using RFID chip mounted on the proximal end of the catheter for communicating catheter information to the operation console to select the appropriate classification tree. Those skilled in the art will realize that the same methods may be implemented by a system for characterizing vascular tissue data using different methods of storing, transferring and receiving data between the catheter and operation console. At step 401, data regarding the identification and operating characteristics of the catheter is stored on an RFID chip located on the proximal end of the catheter. This may include one or more of the catheter serial number, catheter name, catheter model number, calibration coefficients, time gain control, post amp gain, date of first use, date of last use, number of times used, number of permissible uses, geographic location of permissible use, boot mode, pulse width, or expiration date of the catheter to the operation console.

At step 402, the catheter is connected to an interface device. For example, the interface device may be a pullback device, such as the Volcano™ Revolution™ PIM, or the Volcano™ R100, for operation of a rotational or phased array IVUS catheter. The connection between the catheter and the interface device activates the interface device, and at step 403, an RFID scanner on the interface device reads the catheter identification and operating data stored on the catheter RFID chip. The interface device may further comprise a microprocessor for initially processing some of the data from the RFID chip, or the interface device may simply relay the information to the operation console for processing. For example, at step 404, the interface device may read a security code or expiration date stored on the RFID chip and if the security code is not authorized or the expiration date has passed, at step 405 the interface device may prohibit operation of the catheter.

At step 406, the interface device transfers the information from the catheter RFID chip to the attached operation console using a standard communication protocol, such as USB or serial. At step 407, the operation console uses this data to select one of multiple VH classification trees for analyzing data received from that catheter. For example, the operation console may use data regarding the catheter model number to determine whether the catheter is a phased array or rotational IVUS catheter. The operation console may then use the data regarding the catheter operating frequency to select the classification tree corresponding to that catheter type with that operating frequency.

At step 408, the interface device operates the catheter to collect IVUS data from the imaging element located in the patient's vasculature. The interface device may use information regarding the catheter performance characteristics that was stored on the RFID chip, for example the catheter boot mode, to operate the catheter. The IVUS data is transmitted to the operation console where it is processed and analyzed. Once again, the operation console may use information received from the catheter RFID chip to process and optimize the IVUS data, e.g. RF backscatter data. For example, the time gain control, post amp gain and pulse width data regarding the catheter signal stored on the RFID chip may be used to process IVUS data.

At step 409, the spectral parameters of the IVUS data are identified and compared to parameters stored in the VH classification tree for each of the known tissue types, including fibrous tissue, fibro-fatty, necrotic core, dense calcium, thrombus, organized thrombus, blood, highly vascular tissue and not highly vascular tissue. In addition, non-tissue material, such as stent material, can also be identified. In areas where the signal is too low to characterize tissue with a high level of confidence, the image can be blacked out to avoid misinterpretation of the image. The same process can also be used in other applications to identify myocardium or cancer cells. At step 410, if a match (either exactly or substantially) is found, the region related with that parameter is correlated to the tissue type stored in the VH classification tree.

At step 411, once the clinical procedure is complete, the information regarding the characterization of the tissue is downloaded to the RFID chip via the interface device. In addition, the operation console may transmit additional information regarding the procedure, including for example patient identification, operating physician, hospital information, time and duration of procedure, etc. In this way, the RFID chip could be used as a complete medical record of the procedure.

Having thus described a preferred embodiment of a method and system for characterizing vascular tissue, it should be apparent to those skilled in the art that certain advantages of the within system have been achieved. It should also be appreciated that various modifications, adaptations, and alternative embodiments thereof may be made within the scope and spirit of the present invention. For example, a system using an RFID device for communication between the catheter and operation console has been illustrated, but it should be apparent that the inventive concepts described above would be equally applicable for any number communication methods between the catheter and operation console. In addition, the invention is not limited to a particular type of IVUS catheter, and may be used in the characterization of IVUS data from rotational as well as phased array IVUS catheters. The invention is defined by the following claims.

We claim:

1. A method, comprising:
providing a catheter having an RFID chip located on a connector configured to interface with a catheter interface device, the connector being at a proximal end of the catheter, and the catheter further having a transducer adjacent a distal end of the catheter, the RFID chip storing information related to a function of the catheter;
accessing information related to the function of the catheter stored on the RFID chip using an RFID scanner of the catheter interface device, wherein the accessing includes activating the RFID scanner in response to the connector being inserted into the catheter interface device such that the RFID scanner is activated to access the information stored on the RFID chip, wherein the catheter interface device is a pullback device configured to control longitudinal movement of the catheter, including the transducer, through a vessel;
identifying at least one operating characteristic related to the function of the catheter based on the information related to the function of the catheter accessed from the RFID chip, the at least one operating characteristic including an operating parameter of the transducer; and
using the at least one operating characteristic related to the function of the catheter to control operation of the transducer.

2. The method of claim 1, wherein the at least one operating characteristic related to the function of the catheter is selected from a group of operating characteristics consisting of catheter serial number, catheter name, catheter make, catheter model, calibration coefficients, time gain control, post amp gain, date of first use, date of last use, number of uses, hours of use, boot mode, pulse width, expiration date, number of permissible uses, hours of permissible use, geographic region of permissible use, failure codes, and patient information.

3. The method of claim 2, further comprising:
prohibiting use of the catheter based on the at least one operating characteristic related to the function of the catheter.

4. The method of claim 1, wherein the at least one operating characteristic related to function of the catheter includes at least one of a transducer type or a transducer frequency.

5. The method of claim 1, further comprising communicating the at least one operating characteristic related to the function of the catheter to an operation console.

6. The method of claim 5, wherein the communicating the at least one operating characteristic related to the function of the catheter to an operation console includes wirelessly communicating with the operation console.

7. The method of claim 5, further comprising communicating additional information related to the function of the catheter to the operation console.

8. The method of claim 1, further comprising updating the information related to the function of the catheter stored on the RFID chip.

9. The method of claim 8, further comprising monitoring catheter operation, wherein the updating the information related to the function of the catheter stored on the RFID chip includes updating based on monitoring catheter operation.

10. The method of claim 8, wherein updating the information comprises saving data from an operation console onto the RFID chip.

11. The method of claim 8, wherein updating the information comprises writing to a memory of the RFID chip using the RFID scanner.

12. A catheter system, comprising:
a catheter interface device configured to interface with a connector located at a proximal portion of a catheter including a transducer at a distal portion and an RFID chip storing data representative of at least one operating characteristic related to a function of the catheter located on the connector, the at least one operating characteristic including an operating parameter of the transducer,
wherein the catheter interface device is a pullback device configured to control longitudinal movement of the catheter, including the transducer, through a vessel, and
wherein the catheter interface device further includes an RFID scanner configured to retrieve the data representative of at least one operating characteristic related to a function of the catheter stored on the RFID chip, wherein the RFID scanner is activated in response to the connector being inserted into the catheter interface device such that the RFID scanner is activated to access information stored on the RFID chip.

13. The system of claim 12, further comprising:
an operation console in communication with the catheter interface device, the operation console configured to obtain the at least one operating characteristic related to the function of the catheter from the catheter interface device and utilize the obtained at least one operating characteristic related to the function of the catheter to control operation of the transducer.

14. The system of claim 13, wherein the operation console is in wireless communication with the catheter interface device.

15. The system of claim 13, wherein the operation console is spaced from the catheter interface device.

16. The system of claim 13, wherein at least one of the interface device or the operation console is operable to prohibit use of the catheter based on the at least one operating characteristic related to the function of the catheter.

17. The system of claim 12, wherein the at least one operating characteristic related to the function of the catheter is selected from a group of operating characteristics consisting of catheter serial number, catheter name, catheter make, catheter model, calibration coefficients, time gain control, post amp gain, date of first use, date of last use, number of uses, hours of use, boot mode, pulse width, expiration date, number of permissible uses, hours of permissible use, geographic region of permissible use, failure codes, and patient information.

18. The method of claim 12, wherein the at least one operating characteristic related to function of the catheter includes at least one of a transducer type or a transducer frequency.

19. The system of claim 12, wherein the RFID scanner is an RFID reader.

20. The system of claim 12, wherein the RFID scanner is a read/write scanner.

21. The system of claim 12, wherein the RFID chip is disposed on a sidewall of the connector.

22. An intravascular system, comprising:
an intravascular device sized and shaped for positioning within a vessel of a patient, a physiologic sensor positioned at a distal portion of the intravascular device, and a RFID chip storing data representative of a number of uses of the intravascular device at a proximal portion of the intravascular;
a pullback device connected to the intravascular device to control longitudinal movement of the intravascular device through the vessel, wherein the pullback device comprises an RFID scanner configured to retrieve the data representative of the number of uses of the intravascular device stored on the RFID chip, wherein the RFID scanner is automatically activated in response to the RFID chip being moved into a position within readable proximity to the RFID scanner when the proximal portion of the intravascular device is inserted into the pullback device such that the RFID scanner is activated to access the information stored on the RFID chip;
an operation console in communication with the RFID scanner, the operation console configured to:
obtain the data representative of the number of uses of the intravascular device stored on the RFID chip from the RFID scanner;
compare the number of uses of the intravascular device to a number of permissible uses of the intravascular device; and
control operation of the physiologic sensor based on the comparison of the number of uses and the number of permissible uses, wherein the controlling includes obtaining physiologic data within the vessel using the physiologic sensor when the number of uses is less than the number of permissible uses and otherwise prohibiting the operation of the physiologic sensor.

\* \* \* \* \*